(12) United States Patent
Schulz

(10) Patent No.: US 12,708,531 B2
(45) Date of Patent: Aug. 18, 2026

(54) METACARPUS ELEMENT WITH VOLUME FOR A HAND PROSTHESIS

(71) Applicant: Stefan Schulz, Karlsruhe (DE)

(72) Inventor: Stefan Schulz, Karlsruhe (DE)

( * ) Notice: Subject to any disclaimer, the term of this patent is extended or adjusted under 35 U.S.C. 154(b) by 853 days.

(21) Appl. No.: 18/000,582

(22) PCT Filed: Jun. 6, 2021

(86) PCT No.: PCT/DE2021/100484
§ 371 (c)(1),
(2) Date: Dec. 2, 2022

(87) PCT Pub. No.: WO2021/244708
PCT Pub. Date: Dec. 9, 2021

(65) Prior Publication Data
US 2023/0210673 A1 Jul. 6, 2023

(30) Foreign Application Priority Data
Jun. 5, 2020 (DE) ........................ 102020115097.0

(51) Int. Cl.
*A61F 2/70* (2006.01)
*A61F 2/54* (2006.01)
*A61F 2/58* (2006.01)
*B25J 19/00* (2006.01)
*A61F 2/50* (2006.01)

(52) U.S. Cl.
CPC .............. *A61F 2/586* (2013.01); *A61F 2/583* (2013.01); *A61F 2/70* (2013.01); *B25J 19/0075* (2013.01); *A61F 2002/5089* (2013.01); *A61F 2002/701* (2013.01)

(58) Field of Classification Search
None
See application file for complete search history.

(56) References Cited

U.S. PATENT DOCUMENTS

2006/0224249 A1 10/2006 Winfrey
2010/0198362 A1* 8/2010 Puchhammer .......... A61F 2/588 623/65
2018/0036145 A1* 2/2018 Jury ...................... A61L 27/165
2021/0085491 A1* 3/2021 Akhtar .................... A61F 2/583

FOREIGN PATENT DOCUMENTS

AU 2016102467 A4 7/2021
DE 101 15 693 A1 10/2002
DE 20 2016 008 877 U1 6/2020
WO 2019/011830 A1 1/2019

OTHER PUBLICATIONS

International Search Report Corresponding to PCT/DE2021/100484 mailed Dec. 1, 2021.
Written Opinion Corresponding to PCT/DE2021/100484 mailed Dec. 1, 2021.

* cited by examiner

*Primary Examiner* — David H Willse
(74) *Attorney, Agent, or Firm* — Secant IP, P.L.L.C.

(57) ABSTRACT

Metacarpus element for a hand prosthesis,
wherein the metacarpus element comprises at least one connecting element for connecting the metacarpus element to at least one finger frame element, and wherein the metacarpus element comprises a basic metacarpus body and a metacarpus cover, and the basic metacarpus body, together with the metacarpus cover, define a volume.

9 Claims, 8 Drawing Sheets

1
2
3
4
5
6
7
8
9
10
11
12
14
15
16
17
18
19
20
22
23
24
25
26
27
28
30
31
32
33
34
35
36
38
39
39a
39b
39c
39d
40
41
42
43
44
45
46
200
200

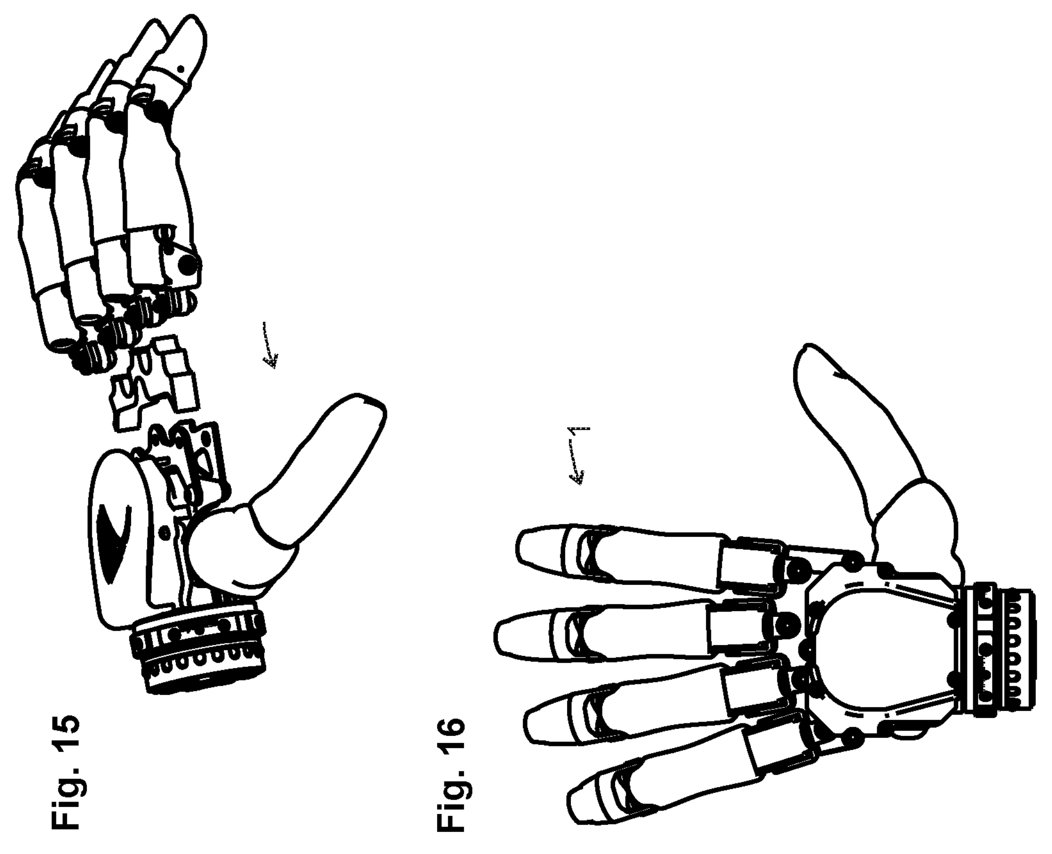
Fig. 15
Fig. 16
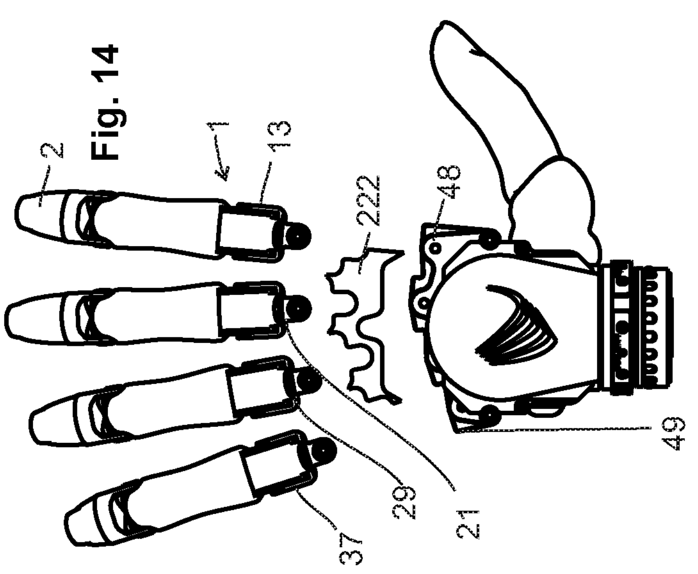
Fig. 14

METACARPUS ELEMENT WITH VOLUME FOR A HAND PROSTHESIS

FIELD OF THE INVENTION

The invention relates to a metacarpus element for a hand prosthesis and to a hand prosthesis comprising a metacarpus element.

PRIOR ART

Hand prostheses are used to replicate natural hands or the function of natural hands. For this, hand prostheses comprise a number of finger elements, which can comprise several phalanges. The finger elements can for example be moved by means of one or more electric motors. The said motor can be located in the phalanx, in particular in the first phalanx. Furthermore, the hand prosthesis can comprise a thumb element which has a number of thumb phalanges. The finger elements and the thumb element can be connected to one another by way of a palm element. Via the palm element the finger elements and the thumb element can also be connected to a wrist element. Hand prostheses can be adapted to suit the use concerned. Thus, various sizes and shapes of hand prostheses can be made. Moreover, in modern hand prostheses the left-hand prosthesis differs in its shape from the right-hand prosthesis. Thus, the left hand prosthesis is often mirror-symmetrical relative to the right hand prosthesis.

OBJECTIVE

The purpose of the present invention is to provide a new and inventive hand prosthesis. A further objective can be to design a more robust hand prosthesis.

DESCRIPTION OF THE INVENTION

The stated objective is achieved by a metacarpus element according to the first independent claim and a hand prosthesis according to the further independent claim.

Preferred embodiments are described in the subordinate claims.

The objective is achieved by a metacarpus element for a hand prosthesis, wherein the metacarpus element comprises at least one connecting element for connecting the metacarpus element to at least one finger frame element, characterized in that the metacarpus element has a basic metacarpus body and a metacarpus cover, and the basic metacarpus body and the metacarpus cover define a volume between them.

In this case the metacarpus element is connected directly or indirectly to the finger elements and/or to a thumb element. The metacarpus element can also comprise a receiving structure for a wrist element.

Preferably, the metacarpus element is made from a metal such as aluminum, steel or titanium, and/or a plastic or a composite material such as a carbon-fiber composite material.

The basic metacarpus body can comprise the connecting element for connecting the metacarpus element to the finger elements, in particular by way of the finger frame elements.

In this case the basic metacarpus body can define a first part-volume. The said part-volume can be fully or partially open toward the top. The metacarpus cover can have a second part-volume, such that the second part-volume of the metacarpus cover can be fully or partially open toward the bottom. The volume can be formed by the basic metacarpus body and the metacarpus cover. The metacarpus cover can even be made flat or approximately flat, so that the volume is formed only by the basic metacarpus body. The volume can also be formed by the metacarpus cover alone and the basic metacarpus body delimits the volume downward.

It has also been recognized that a volume can be provided by the metacarpus element, for example for the accommodation of sensitive components such as electrical or electronic control units, or sensors such as position and/or temperature sensors. By virtue of the said volume these components can be protected more effectively against environmental influences such as mechanical and/or electrical and/or magnetic influences.

In particular a seal, particularly a sealing ring, can be fitted between the basic metacarpus body and the metacarpus cover. Thanks to the sealing ring, which in particular is made from a flexible plastic material, the transition between the basic metacarpus body and the metacarpus cover can be sealed better. Thereby, improved impermeability to dust and/or water can be ensured.

In particular the sealing ring can be a closed or an open ring. Preferably, the sealing ring can be fitted into a groove that extends round the volume in the basic metacarpus body. In that way the sealing ring can be fixed in relation to the shape of the basic metacarpus body. In the area of the cable passages the seal can be have a profile adapted to the cable, or alternatively a malleable sealing mass can be used. Preferably the basic metacarpus body is connected detachably to the metacarpus cover. Thus, the basic metacarpus body can be connected to the metacarpus cover in such manner that the metacarpus cover can be removed from the basic metacarpus body without destroying it, and re-connected to the basic metacarpus body.

In particular, the basic metacarpus body is connected to the metacarpus cover by means of screws, or a snap-on closure, or in some other likewise detachable manner.

Preferably, the volume is sealed in a water-tight and/or dust-excluding manner.

The objective is also achieved by a hand prosthesis with a metacarpus element as described above.

In particular the volume can accommodate a prosthesis control unit. Such a control unit, in particular an electric and/or electronic control unit, may be a particularly sensitive component, so that the sealing of the control unit against water and/or dust and/or other environmental influences can make the prosthesis less sensitive.

DESCRIPTION OF THE DRAWINGS

In what follows, the invention will be described in greater detail with reference to example embodiments, with the help of the drawings.

In particular, the objective is achieved by a metacarpus element for a hand prosthesis, wherein the metacarpus element comprises at least one connecting element for connecting the metacarpus element to at least one finger frame element and the metacarpus element is made in such manner that it can be used just as well for a left-hand as for a right-hand hand prosthesis.

Figure 1:
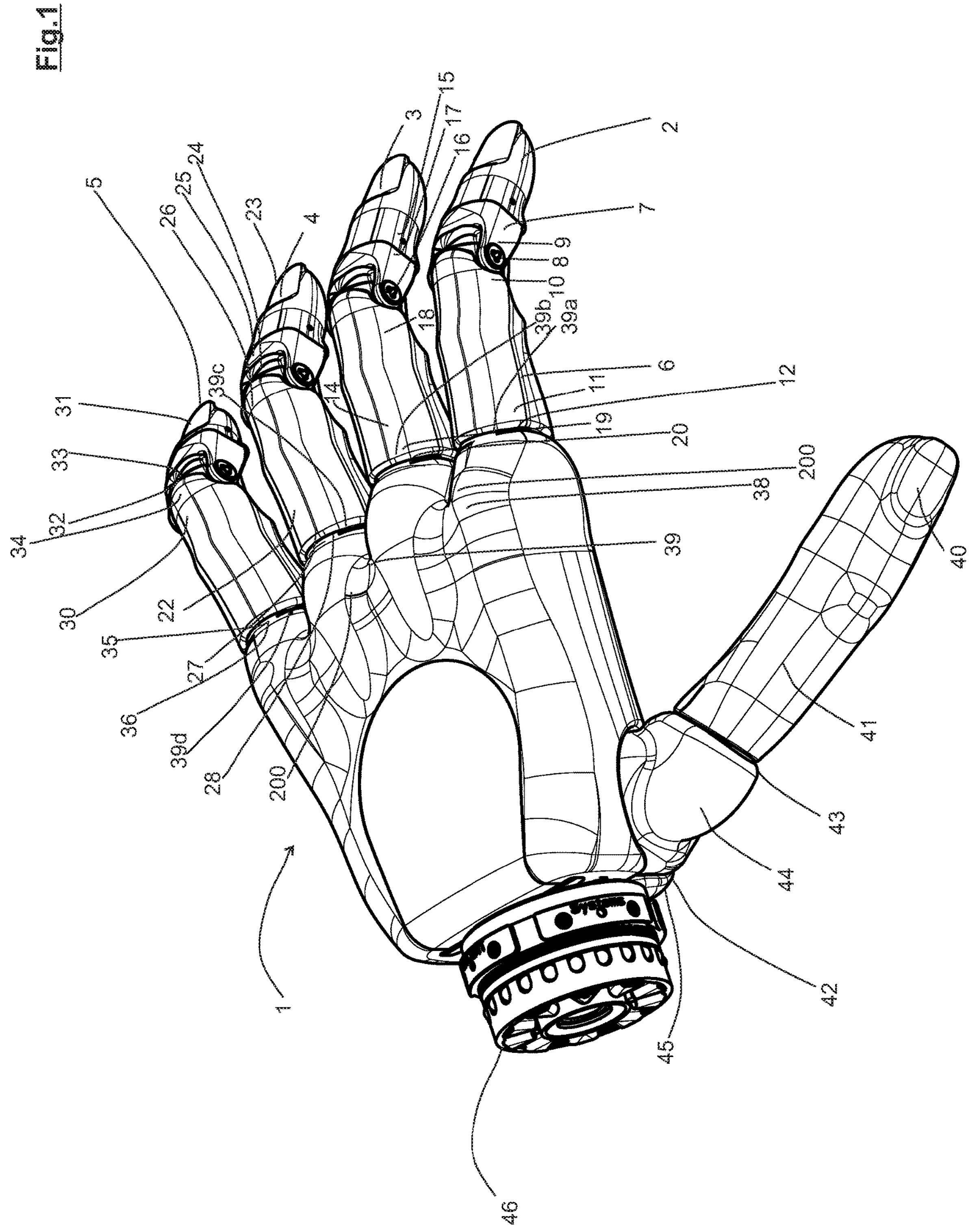

In this context a metacarpus element is understood to mean an element which is connected directly or by way of one or more further elements to the thumb element and to one or more finger elements. Preferably the metacarpus element is between the thumb element and one or more finger elements. Also preferably, the metacarpus element is between the thumb element and one or more finger elements and the wrist element.

In particular the metacarpus element can be located between one or more finger frame elements and the wrist element and/or the thumb element.

Preferably the metacarpus element is part of the palm element, such that the palm element can correspond to the palm and/or the metacarpus of the human hand. Preferably, the palm element comprises the metacarpus element and the finger frame element.

Thus, it was recognized that the metacarpus element is suitable to be designed in such manner that it can be used for both a left-hand and a right-hand hand prosthesis. This can also apply when the left-hand hand prosthesis is not made identically with the right-hand hand prosthesis, for example when the left-hand prosthesis is a mirror image of the right-hand prosthesis. Thus, the metacarpus element can for example be designed symmetrically, in particular axis-symmetrically.

A connecting element is understood to mean an element that enables the connection, in particular the detachable connection of the metacarpus element to the finger frame element. Such a connecting element can comprise one or more recesses, screws, threaded bores, one or more holes, one or more projections, etc.

It has been recognized that the connecting element can be arranged in such manner that the metacarpus element can be used both for a right hand prosthesis and for a left hand prosthesis. Thus the number of different metacarpus elements can be reduced since the same metacarpus element can be used both for a right-hand and for a left-hand hand prosthesis.

Preferably, the connecting element is arranged mirror-symmetrically relative to a main axis of the hand prosthesis or the metacarpus element. The main axis can extend in the metacarpus element and/or the hand prosthesis from the distal to the proximal.

The connecting element can comprise at least two connecting part-elements, which relative to one another and to the main axis are arranged symmetrically. Thus, by using a plurality of connecting part-elements a more stable connection can be produced, which owing to its symmetrical arrangement can be used both for a right-hand and for a left-hand hand prosthesis.

It is also possible to use a plurality of connecting elements which are if necessary not arranged symmetrically. In that case a first sub-group of connecting part-elements can be used to connect the metacarpus element for a right-hand hand prosthesis to the finger frame element and a second sub-group of the connecting part-elements can be used to connect the metacarpus element for a left-hand hand prosthesis to the finger frame element. Connecting part-elements can also be elements of both sub-groups, or all the connecting part-elements can be used for connecting the left-hand prosthesis or for connecting the right-hand prosthesis.

The connecting part-elements can be bores and/or threaded bores. Such bores and/or threaded bores can be used in such manner that one or more finger frame elements can be attached to the metacarpus element by means of screws.

Preferably the connecting element is arranged in the distal area of the metacarpus element and so, for example, the finger frame element is arranged on the area of the metacarpus element which is adjacent to the finger elements.

The metacarpus element can comprise a thumb element receiver for holding a thumb element. Thus, the thumb element can be attached to the metacarpus element. The thumb element receiver can in that case comprise a recess into which an element connected to the proximal end of the thumb element, or the proximal end of the thumb element itself, can be introduced from the side. Preferably, the proximal end of the thumb element can be introduced into the recess from both sides. There, the thumb element, in particular at a proximal end, can be connected to the metacarpus element for example by screwing or clamping.

In general the thumb element receiver can be designed such that a thumb element can be arranged both on the left side and on the right side of the metacarpus element.

Preferably, a hand prosthesis comprises a metacarpus element as described above. The hand prosthesis can comprise one or more finger frame elements. Such finger frame elements can be connected on their proximal side to the distal side of the metacarpus element.

The finger frame element can be made flat, in particular as a sheet for example of steel, titanium, plastic or aluminum. On its distal side the finger frame element can be designed with connecting elements for connecting the finger frame element to one or more, preferably four finger elements.

In particular, the finger frame element can be asymmetrical, for example curved or stepped or approximately trapezium-shaped, following the anatomy of the human hand. The size and shape of the finger frame element can be chosen to match the size of the user's hand or of the hand prosthesis and the shape of the user's hand or the shape of the hand prosthesis desired.

The finger frame element can have one or more cut-outs, in order to make the finger frame element particularly flexible and light.

A first finger frame element can be attached respectively to an upper side of the metacarpus element (the side facing toward the back of the hand) and a second finger frame element on an underside of the metacarpus element (the side facing toward the palm). In that case the two finger frame elements can extend in parallel planes. The finger elements can then be attached respectively to both finger frame elements.

Thanks to the parallel arrangement of more than one finger frame element, a lightweight but still torsionally rigid structure can be produced.

Preferably, the metacarpus element is connected to the finger frame element distally, with the finger frame element carrying a plurality of fingers.

DESCRIPTION OF THE DRAWINGS

Below, the invention is described in greater detail with reference to example embodiments, with the help of drawings.

Figures 2, 3, 4, 5, 6:
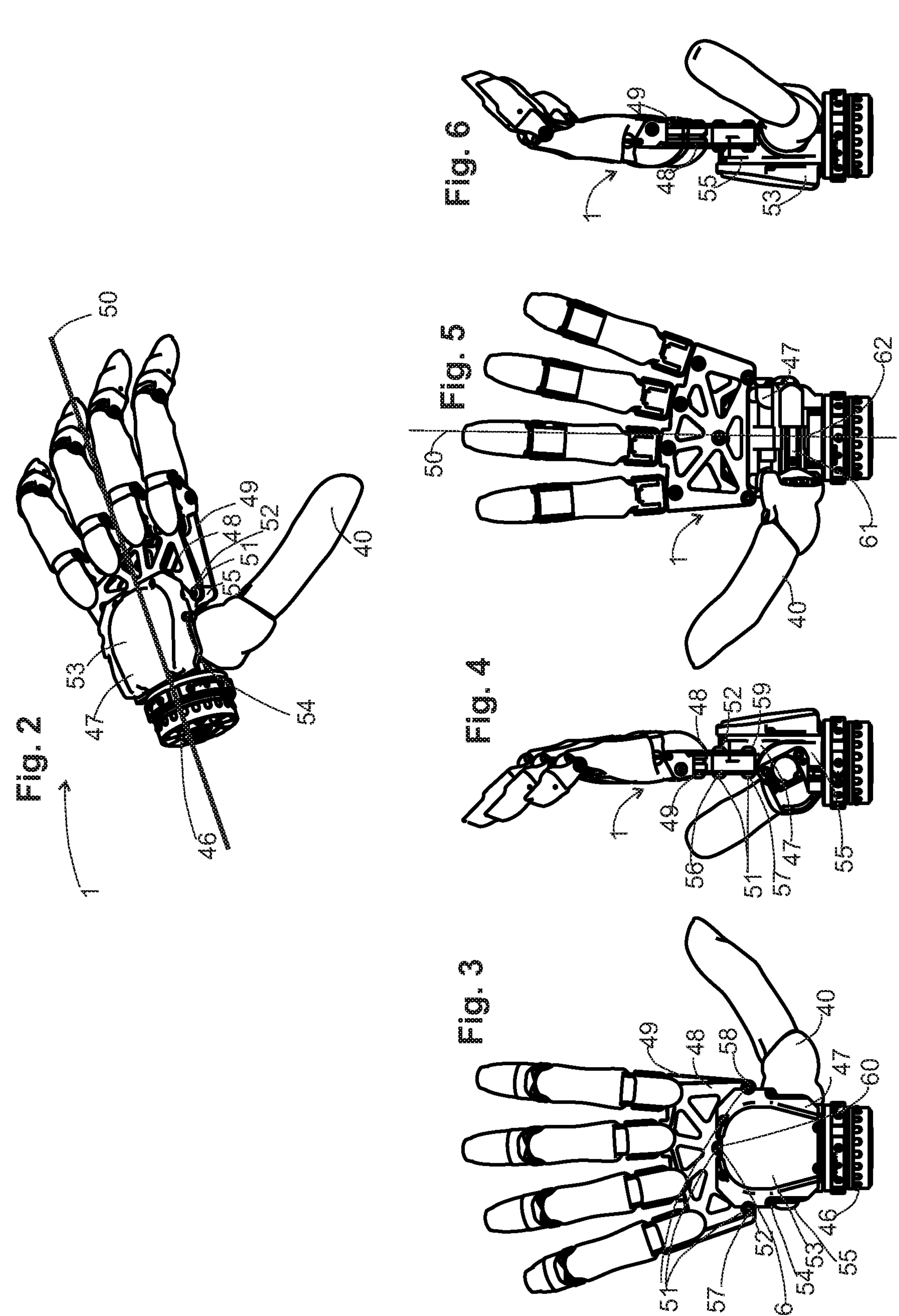

The drawings show:

FIG. 1: A hand prosthesis,

FIG. 2: A hand prosthesis without its covering, viewed laterally from above, FIG. 3: A hand prosthesis without its covering, viewed from above, FIG. 4: A hand prosthesis without its covering, viewed from the left, FIG. 5: A hand prosthesis without its covering, viewed from below, FIG. 6: A hand prosthesis without its covering, viewed from the right, FIG. 7: An exploded view of a hand prosthesis, FIG. 8: An exploded view of the hand prosthesis of FIG. 7, seen from below, FIG. 9: An exploded view of a hand prosthesis with various finger frame elements, FIG. 10: A metacarpus element, FIG. 11: An exploded view of the metacarpus element of FIG. 10, FIG. 12: A metacarpus element, viewed from the front, FIG. 13: A metacarpus element, opened from the front, FIG. 14: An exploded view of a hand prosthesis with movement dampers, FIG. 15: The hand prosthesis of FIG. 14, viewed from the side, FIG. 16: The hand prosthesis of FIG. 14, viewed from below, FIG. 17: A sectioned view of a finger element.

FIG. 1 shows a hand prosthesis 1 with a first finger element 2, a second finger element 3, a third finger element 4 and a fourth finger element 5. The first finger element 2 comprises a first proximal phalanx 6 and a first distal phalanx 7. In this case the first distal phalanx 7 is connected to a distal end 10 of the first proximal phalanx 6 in such manner that it can pivot by way of a first distal interphalangeal joint 8 at a proximal end 9 of the first distal phalanx 7. A proximal end 11 of the first proximal phalanx 6 is connected by means of a first proximal interphalangeal joint 12 to a first phalanx base member 13 (not shown here).

The second finger element 3 comprises a second proximal phalanx 14 and a second distal phalanx 15. Here, the second distal phalanx 15 is connected to a distal end 18 of the second proximal phalanx 14 in such manner that it can pivot by way of a second distal interphalangeal joint 16 at a proximal end 17 of the second distal phalanx 15. A proximal end 19 of the second proximal phalanx 14 is connected by means of a second proximal interphalangeal joint 20 to a second phalanx base member 21 (not shown here).

The third finger element 4 comprises a third proximal phalanx 22 and a third distal phalanx 23. Here, the third distal phalanx 23 is connected to a distal end 26 of the third proximal phalanx 22 in such manner that it can pivot by way of a third distal interphalangeal joint 24 at a proximal end 25 of the third distal phalanx 23. A proximal end 27 of the third proximal phalanx 22 is connected by means of a third proximal interphalangeal joint 28 to a third phalanx base member 29 (not shown here).

The fourth finger element 5 comprises a fourth proximal phalanx 30 and a fourth distal phalanx 31. In this case the fourth distal phalanx 31 is connected to a distal end 34 of the fourth proximal phalanx 30 in such manner that it can pivot by way of a fourth distal interphalangeal joint 32 at a proximal end 33 of the fourth distal phalanx 31. A proximal end 35 of the fourth proximal phalanx 30 is connected by means of a fourth proximal interphalangeal joint 36 to a fourth phalanx base member 37 (not shown here).

The hand prosthesis further comprises a sheath 38 made from a soft plastic material such as silicone. In this case the sheath 38 at least partially covers the proximal interphalangeal joints 12, 20, 28, 36 for example, in order to prevent any object from making its way into the proximal interphalangeal joints 12, 20, 28, 36 or between a palm element 200 and one of the proximal phalanxes 6, 14, 22, 30.

The sheath 38 has in its distal area 39 four openings 39*a, b, c, d*. In this case the first finger element 2 projects through a first opening 39*a*, the second finger element 3 through the second opening 39*b*, the third finger element 4 through the third opening 39*c* and the fourth finger element 5 through the fourth opening 39*d*. The openings 39*a*, 39*b*, 39*c*, 39*d* can be arranged approximately in a row corresponding to the anatomical position of the metacarpo-phalangeal joints. The openings 39*a, b, c, d* can comprise the corresponding finger elements 2, 3, 4, 5 in the proximal area and in that way, for example, can damp or restrict a movement of the proximal area relative to the palm element 200. In particular a pivoting movement of one or more of the finger elements 2, 3, 4, 5 in a main plane of the palm element 200 can be damped by the sheath 38.

The hand prosthesis 1 also comprises a thumb element 40 with a distal thumb phalanx 41 and a proximal thumb phalanx 42. The thumb element 40 can also pass though an opening in the sheath 38, or the sheath 38 does not cover the thumb element so that the sheath 38 can be pulled over the palm element 200.

In this case the distal thumb phalanx 41 is connected to the proximal thumb phalanx 42 by a distal thumb joint 43 and is covered by a cap 44. The cap 44 is approximately tubular with two opposite openings, such that the distal thumb phalanx 41 extends through one opening and the proximal thumb phalanx 42 through the second opening. Thus, the cap 44 is held in place by the two thumb phalanges 41 and 42 and the thumb joint 43.

At the proximal end 45 of the hand prosthesis 1 there is a wrist joint element 46 which can be connected to the stump of an arm.

FIG. 2 shows the hand prosthesis 1 without its sheath 38, viewed obliquely from above. The hand prosthesis 1 comprises a metacarpus element 47 which is connected to the wrist element 46, a first finger frame element 48, a second finger frame element 49 and the thumb element 40. The metacarpus element 47 is in this case mirror-symmetrical relative to the main axis 50 of the metacarpus element 47. The main axis 50 of the metacarpus element 47 extends from the proximal toward the distal.

The metacarpus element 47 has a connecting element 51 for connecting the palm element 47 to the finger frame elements 48, 49. Here, the connecting element 51 consists of a bore through which a screw 52 is inserted.

The metacarpus element 47 has a metacarpus cover 53 which is connected, for example by the screw connection 54, to a basic metacarpus element 55.

The basic metacarpus element 55 and/or the metacarpus cover 53 can be made at least partially from a rigid material such as metal, plastic and/or a composite. In particular the basic metacarpus element 55 and/or the metacarpus cover 53 can be partially transparent.

FIG. 3 shows the hand prosthesis 1 viewed from above without its sheath 38. FIG. 4 shows the hand prosthesis 1 viewed from the right-hand side. It can be seen that the finger frame element 48 and the finger frame element 49 are connected by the connecting element 51 to the metacarpus element 47, in particular to the basic metacarpus element 55. Here, the connecting element 51 comprises connecting part-elements 56, 57, 58 in each case in the form of bores. Through the said connecting part-elements 56, 57, 58, respective screws 52, 59 and 60 are inserted.

FIG. 5 shows the hand prosthesis 1 viewed from below. It can be seen that a thumb-holding member 61 is held in a thumb holder 62. In this case the thumb holder 62 is mirror-symmetrical relative to the main axis 50, so that the thumb element 40 can be attached to the metacarpus element 47 both from the right and from the left side.

FIG. 6 shows the hand prosthesis 1 viewed from the left side. Here the metacarpus cover 53 can be seen, which is attached to the basic metacarpus element 55. It can also be seen that the finger frame elements 48, 49 extend in parallel planes in particular parallel to the main plane of the palm element 200 and are attached to the basic metacarpus element 55.

Figures 7, 8:
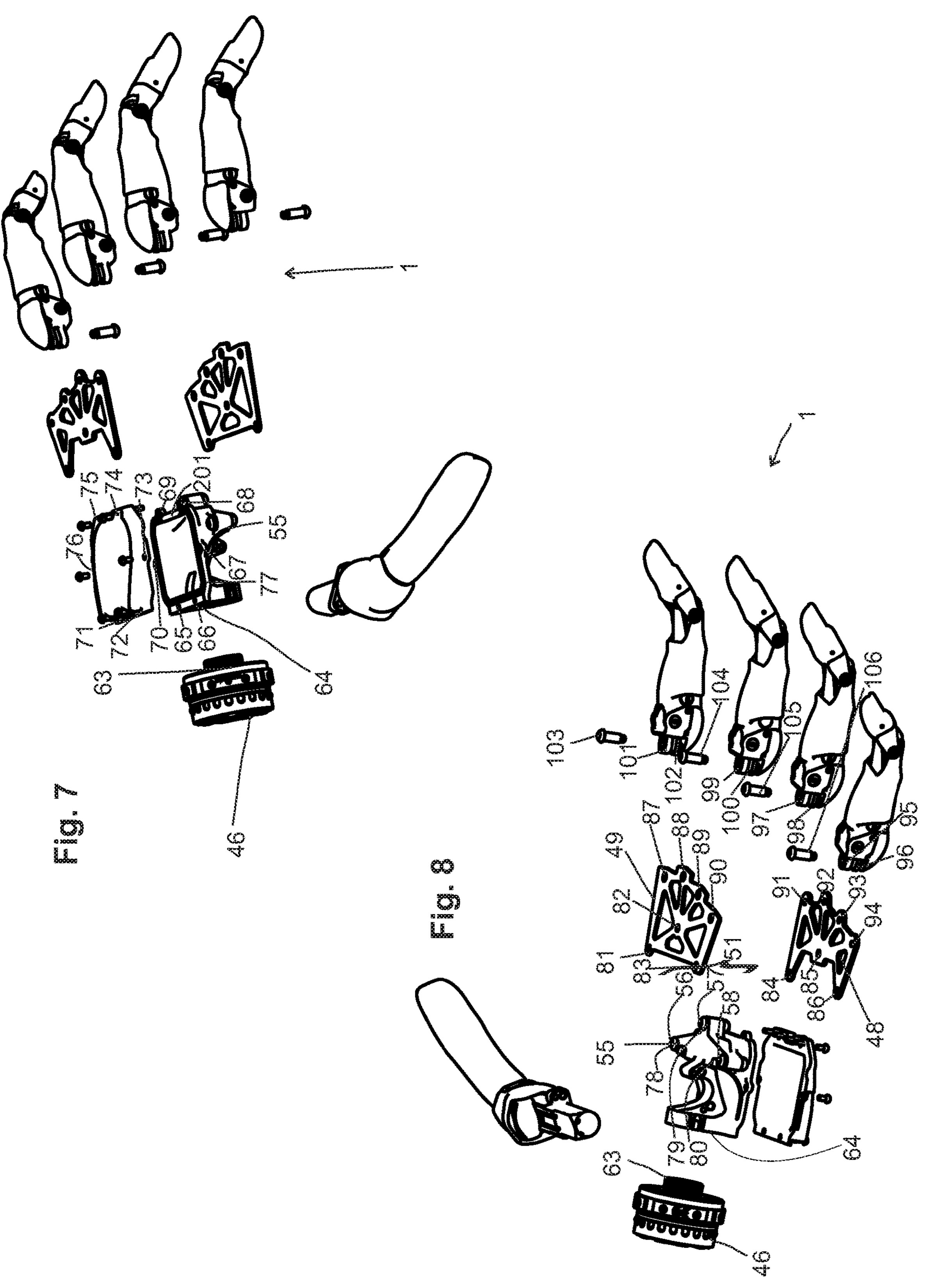

FIGS. 7 and 8 show exploded views of the hand prosthesis 1. Here, the hand prosthesis 1 comprises the basic wrist joint element 46 which can be attached to the basic metacarpus element 55 by way of a cylindrical projection 63. The said projection 63 is introduced into an opening 64 with a similar or if necessary slightly larger diameter then the projection 63. Through bores which lead from outside through the basic metacarpus element 55 to the opening 64, screws can be inserted to hold the projection 63 in the opening 64 and thereby connect the wrist joint element 46 to the basic metacarpus element 55.

The basic metacarpus element 55 has a plurality of threaded bores 65, 66, 67, 68, 69, 70 which correspond to the positions of bores 71, 72, 73, 74, 75, 76 in the metacarpus cover 53. Through the said bores 71, 72, 73, 74, 75, 76 screws can be inserted into the threaded bores 65, 66, 67, 68, 69, 70 so as to connect the basic metacarpus element 55 to the metacarpus cover 53. In this case a seal 77 is arranged between the basic metacarpus element 55 and the metacarpus cover 53, which seals the gap between the basic metacarpus element 55 and the metacarpus cover 53. In its distal area the seal 77 has a gap 201, through which cables can be passed. These cables can serve to deliver electric signals to one or more motors to move one or more of the finger elements. The cables can also supply the one or more motors with current.

In addition the basic metacarpus element 55 comprises the connecting element 51 with its connecting part-elements 56, 57 and 58. These connecting part-elements 56, 57 and 58 are bores through which screws 78, 79 and 80 are inserted. The arrangement of the connecting part-elements 56, 57 and 58 corresponds to the arrangement of the bores 84, 85, 86 of the first finger frame element 48 and the arrangement of the bores 81, 82, 83 in the second finger frame element 49. The screws 78, 79, 80 can for example have a thread and be held in a thread of the bores 84, 85, 86 or 81, 82, 83, or be connected by a nut on the opposite side so that the first finger frame element 48, the basic metacarpus element 55 and the second finger frame element 49 are held between the screw head and the nut. The basic metacarpus element 55 is arranged between the first finger frame element 48 and the second finger frame element 49.

In their distal area the finger frame elements 48 and 49 each have finger element holding bores 91, 92, 93, 94 and 87, 88, 89, 90 respectively. The finger element holding bores 91, 92, 93, 94 of the first finger frame element 48 are spaced apart at the same distance as the finger element holding bores 87, 88, 89, 90.

At the proximal end of the finger elements 2, 3, 4, 5 there is in each case a first tongue 95, 97, 99, 101 and a second tongue 96, 98, 100, 102. Each of the tongues has an opening through which in each case a screw 103, 104, 105, 106 can be inserted. The screws 103, 104, 105, 106 have a cylindrical screw shank provided wholly or partially with a thread and a screw head arranged at the end of the screw shank. In addition, the screws 103, 104, 105 and 106 each have a nut that can be screwed onto the screw shank, or the thread is in the finger frame element 48 in its bores 91, 92, 93, 94 or in the finger frame element 49 in the bores 87, 88, 89, 90.

In the condition when it is being used the first finger frame element 48 is on the upper side of the second tongues 96, 98, 100, 102 and the second finger frame element 49 is on the underside of the first tongues 95, 97, 99 and 101.

The first finger frame element 48 is thus arranged between nuts, which can be omitted if there are threaded bores 87, 88, 89, 90, and the second tongues 96, 98, 100, 102, and the second finger frame element 49 is between the screw heads and the first tongues 95, 97, 99 101.

The finger elements 2, 3, 4, 5 can pivot about an axis which is perpendicular to the planes of the finger frame elements 48, 49 and which corresponds to the main axes of the screws 103, 104, 105, 106. The pivoting movement can be damped by the sheath 38. Moreover, above a certain amplitude of the pivoting movement the basic finger member of each respective finger element 2, 3, 4, 5 encounters one or both finger frame elements 48, 49 as a stop, so that the pivoting movement of the finger element 2, 3, 4, 5 is restricted. During this the maximum amplitude of the pivoting movement differs in size depending on the position of the finger element 2, 3, 4, 5, i.e. whether for example its position corresponds to the first finger element 2, the index finger, or its position corresponds to the middle finger. Also, the maximum amplitude of the pivoting movement in one direction can differ from the maximum amplitude of the pivoting movement in the other direction. The neutral position of the finger element is determined by a finger guide or by the openings 39*a*, 39*b*, 39*c*, 39*d* of the sheath 38.

Figure 9:
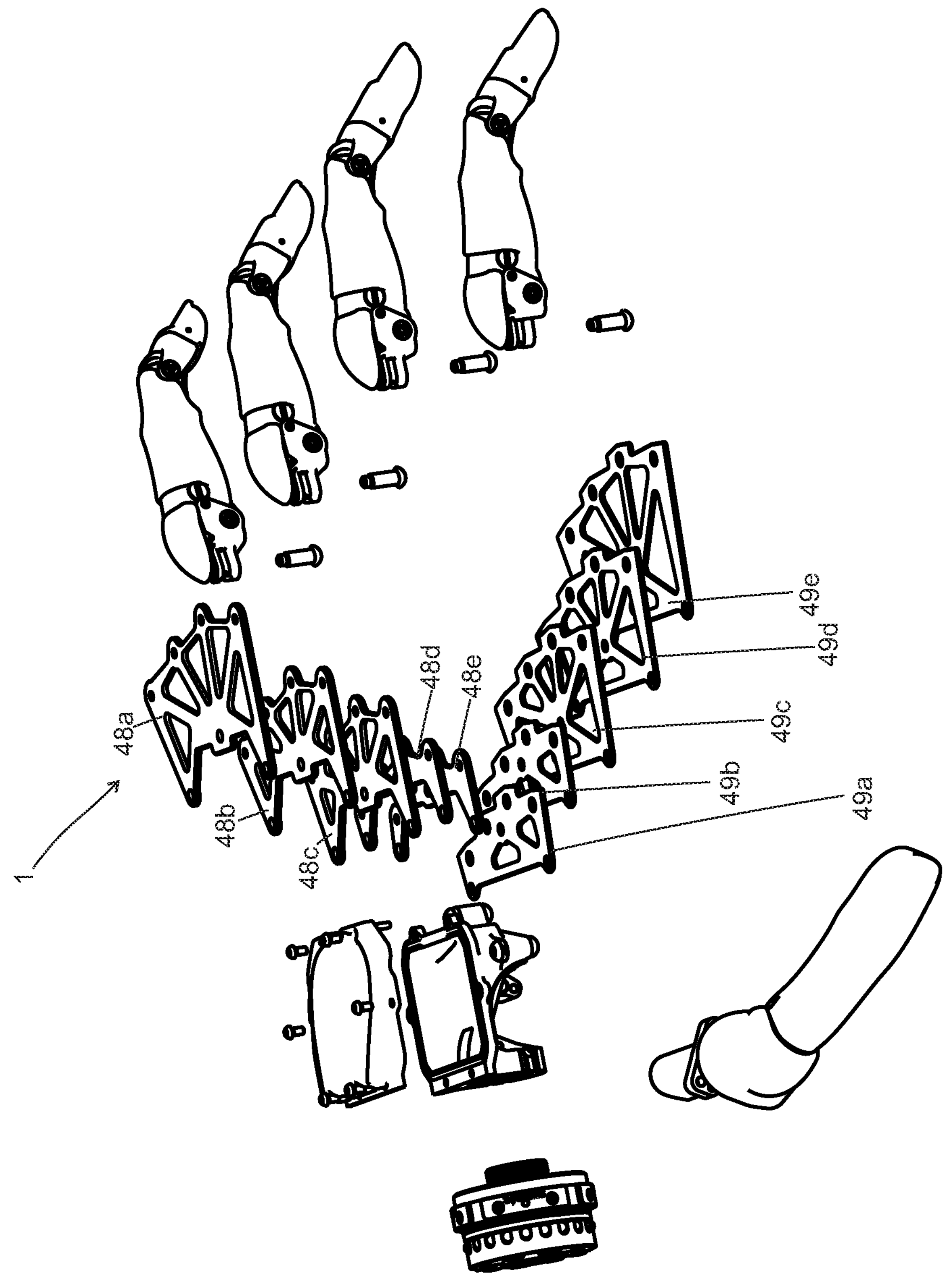

FIG. 9 shows an exploded view of the hand prosthesis 1 with finger frame elements 48*a*, 48*b*, 48*c*, 48*d*, 48*e*, 49*a*, 49*b*, 49*c*, 49*d*, 49*e* of various sizes. Here, it can be seen that by virtue of the various sizes, the connecting elements for connecting the finger frame elements 48, 49 to the basic metacarpus element remain the same, and in particular the position of the bores of the finger frame elements 48, 49 correspond to the connecting part-elements.

The second finger frame elements 49*a, b, c, d, e* have various sizes and each comprises the stop for restricting the pivoting movement.

The first finger frame element 48*a* is used with the second finger frame element 49*a*, the first finger frame element 48*b* is used with the second finger frame element 49*b*, and so on.

Figure 10:
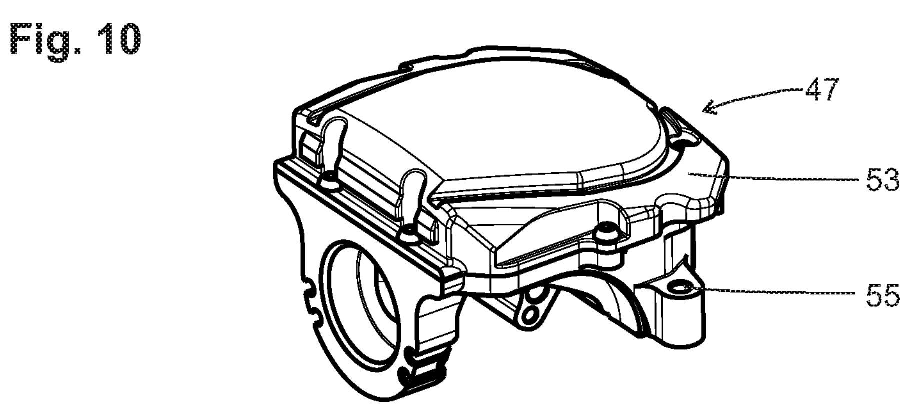
Figure 11:
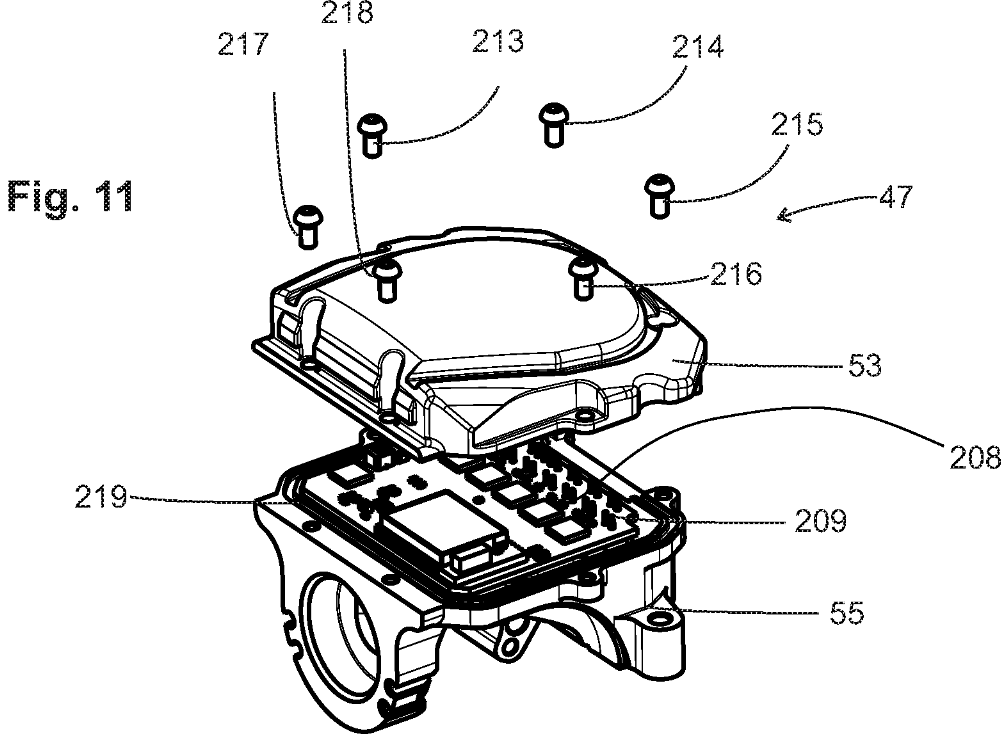

FIG. 10 shows a metacarpus element 47 and FIG. 11 an exploded view of the metacarpus element 47. One can see the metacarpus cover 53 which is attached to the basic metacarpus element 55 by screws 214, 215, 216, 217 and 218. Between the metacarpus cover 53 and the basic metacarpus element 55 is arranged a seal 219, in particular a closed or open sealing ring. In this case the metacarpus cover 53 together with the basic metacarpus element 55 enclose a volume 208 which accommodates a control unit 209. In that way the control unit 209 can be protected against water.

Figure 12:
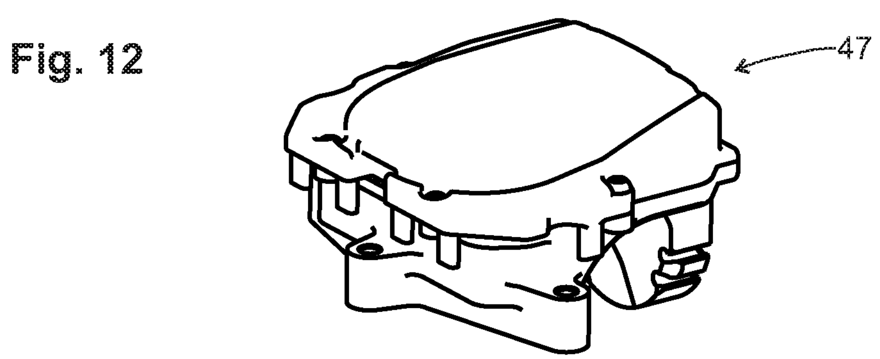

FIG. 12 shows the metacarpus element 47 in a closed condition.

Figure 13:
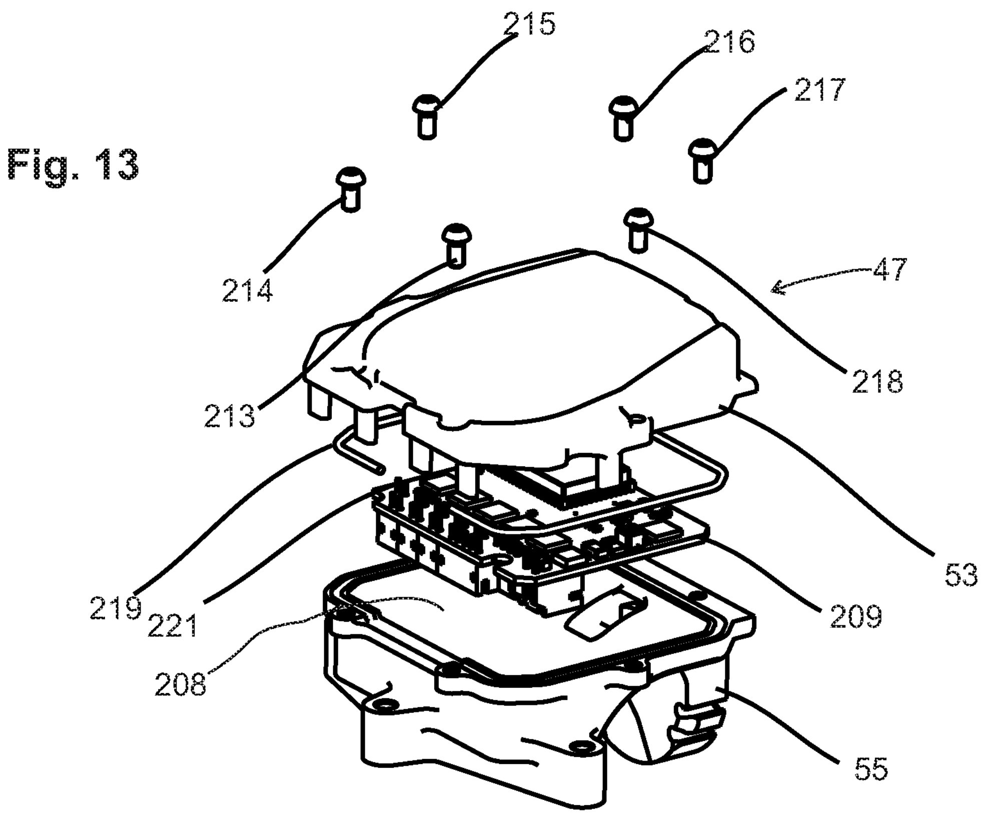

FIG. 13 shows an exploded view of the metacarpus element 47.

In this case the metacarpus cover 53 can be seen together with the basic metacarpus element 55. Between the metacarpus cover 53 and the basic metacarpus element 55 there is the seal 219, in particular a sealing ring for example made from silicone. The seal 219 has a passage opening 221 for cables, through which cables can be passed out from the control unit. In the area of the cable passageway the seal 219 can have a gap and the cables passing through can be held in place by a gel which does not dissolve in water. Thus, the volume 208 remains sealed.

FIG. 14 shows a hand prosthesis 1 with a movement damper 222. In this case the movement damper 222 is held between the basic finger elements 13, 21, 29 and 31 and the finger frame elements 48, 49. The movement damper 222 is made from a flexible material such as rubber or silicone and is in contact with the basic finger elements 13, 21, 29 and 31 so that the basic finger elements 13, 21, 29 and 31 are pushed to a neutral pivoting position and a pivoting movement of the finger element 2 in the main plane of the hand prosthesis 1 (here, the plane of the drawing) is damped.

FIG. 15 shows the hand prosthesis 1 of FIG. 14 viewed from the side.

FIG. 16 shows the hand prosthesis 1 of FIG. 14 viewed from below.

Figure 17:
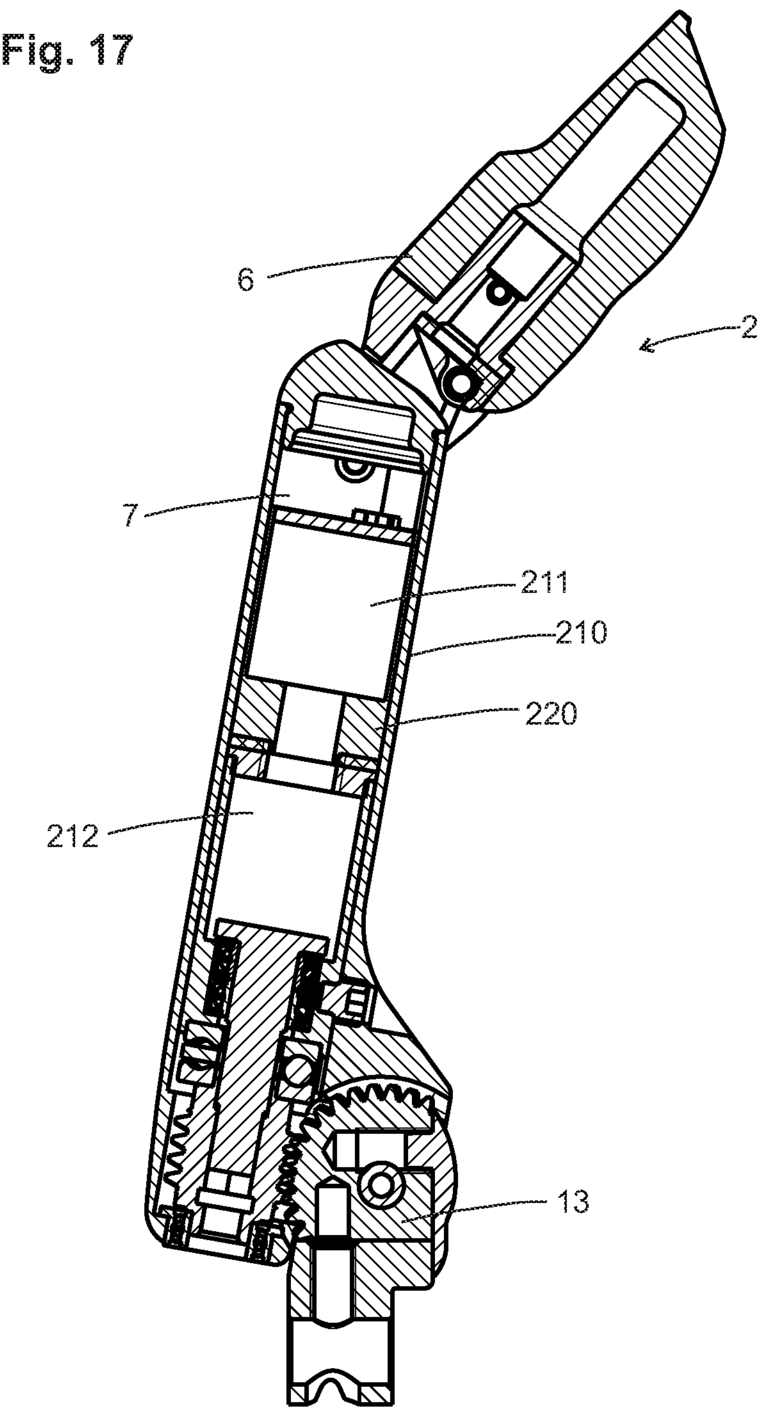

FIG. 17 shows a finger element 2 in a sectioned view seen from the side. Here, the finger element 2 comprises the distal phalanx 6, the proximal phalanx 7 and the basic finger member 13. The proximal phalanx 7 has a sheath 210 inside which an electric motor 211 connected to a transmission 212 is accommodated. The sheath also comprises a water-insoluble gel 220 which at least partially encloses the electric motor 211 and the transmission 212 and therefore seals off at least the electric motor 211 in a watertight manner.

In this case the gel 220 can be fed into the sheath 210 in liquid form while the electric motor 211 and the transmission 212 are already inside the sheath. The gel 220 can then harden and thus seal the sheath 210 at least partially in a watertight and/or dust-tight manner.

INDEXES

1 Hand prosthesis
2 First finger element
3 Second finger element
4 Third finger element
5 Fourth finger element
6 First proximal phalanx
7 First distal phalanx
8 First distal interphalangeal joint
9 Proximal end of the first distal phalanx
10 Distal end of the first proximal phalanx
11 Proximal end of the first proximal phalanx
12 First proximal interphalangeal joint
13 First phalanx base member
14 Second proximal phalanx
15 Second distal phalanx
16 Second distal interphalangeal joint
17 Proximal end of the second distal phalanx
18 Distal end of the second proximal phalanx
19 Proximal end of the second proximal phalanx
20 Second proximal interphalangeal joint
21 Second phalanx base member
22 Third proximal phalanx
23 Third distal phalanx
24 Third distal interphalangeal joint
25 Proximal end of the third distal phalanx
26 Distal end of the third proximal phalanx
27 Proximal end of the third proximal phalanx
28 Third proximal interphalangeal joint
29 Third phalanx base member
30 Fourth proximal phalanx
31 Fourth distal phalanx
32 Fourth distal interphalangeal joint
33 Proximal end of the fourth distal phalanx
34 Distal end of the fourth proximal phalanx
35 Proximal end of the fourth proximal phalanx
36 Fourth proximal interphalangeal joint
37 Fourth phalanx base member
38 Sheath
39 Distal area of the sheath
40 Thumb element
41 Distal thumb phalanx
42 Proximal thumb phalanx
43 Distal thumb joint
44 Cap
45 Proximal end of the hand prosthesis
46 Wrist element
47 Metacarpus element
48 First finger frame element
49 Second finger frame element
50 Main axis of the metacarpus element
51 Connecting element
52 Screw
53 Metacarpus cover
54 Screw connection
55 Basic metacarpus element
56 Connecting part-element
57 Connecting part-element
58 Connecting part-element
59 Screw
60 Screw
61 Thumb-holding member
62 Thumb holder
63 Projection
64 Opening
65 Threaded bore
66 Threaded bore
67 Threaded bore
68 Threaded bore
69 Threaded bore
70 Threaded bore
71 Bore
72 Bore
73 Bore
74 Bore
75 Bore
76 Bore
77 Seal
78 Screw
79 Screw
80 Screw
81 Bore
82 Bore
83 Bore
84 Bore
85 Bore
86 Bore
87 Finger element holding bore
88 Finger element holding bore
89 Finger element holding bore
90 Finger element holding bore
91 Finger element holding bore
92 Finger element holding bore
93 Finger element holding bore
94 Finger element holding bore
95 First tongue
96 Second tongue
97 First tongue
98 Second tongue
99 First tongue
100 Second tongue
101 First tongue
102 Second tongue
103 Screw
104 Screw
105 Screw
106 Screw
103 Screw
200 Palm element
201 Gap in the seal
202 Screw

203 Screw
204 Screw
205 Screw
206 Screw
207 Screw
208 Volume
209 Control unit
210 Sheath
211 Electric motor
212 Transmission
213 Screw
214 Screw
215 Screw
216 Screw
217 Screw
218 Screw
219 Seal
220 Gel
221 Cable passage opening

The invention claimed is:

1. A metacarpus element for a hand prosthesis, wherein the metacarpus element comprises at least one connecting element for connecting the metacarpus element to at least one finger frame element, wherein the metacarpus element comprises a basic metacarpus body and a metacarpus cover, and the basic metacarpus body, together with the metacarpus cover, define a volume, a sealing ring is arranged between the basic metacarpus body and the metacarpus cover to seal a gap between the metacarpus body and the metacarpus cover, the sealing ring has a gap that forms a cable passage opening through which cables pass through the gap between the metacarpus body and the metacarpus cover into the defined volume.

2. The metacarpus element according to claim 1, wherein the cable passage opening is on a side of the sealing ring that faces toward the finger elements.

3. The metacarpus element according to claim 2, wherein the cable passage opening is sealed with a water-insoluble mass.

4. The metacarpus element according to claim 1, wherein the basic metacarpus body is connected detachably to the metacarpus cover.

5. The metacarpus element according to claim 4, wherein basic metacarpus body is connected to the metacarpus cover by means of screws.

6. The metacarpus element according to claim 1, wherein the volume is sealed in a watertight manner.

7. A hand prosthesis comprising a metacarpus element according claim 1.

8. The hand prosthesis according to claim 7, wherein the volume accommodates a prosthesis control unit.

9. The hand prosthesis according to claim 8, wherein the hand prosthesis comprises finger elements which can be moved by means of an electric motor, and the electric motor is accommodated in a proximal phalanx and the control unit controls the electric motor.

* * * * *